United States Patent [19]

Runciman

[11] 4,280,637
[45] Jul. 28, 1981

[54] CONSTANT FEED DEVICE

[75] Inventor: Susann I. C. Runciman, 6 Birkdale Crescent, Mount Osmond, South Australia, Australia

[73] Assignees: Susann I. C. Runciman, Mount Osmond; John R. Thompson, Skye, both of Australia

[21] Appl. No.: 75,319

[22] Filed: Sep. 12, 1979

[30] Foreign Application Priority Data

Sep. 15, 1978 [AU] Australia ............................. PD5969
Nov. 17, 1978 [AU] Australia ............................. PD6819

[51] Int. Cl.³ .............................................. B67D 5/32
[52] U.S. Cl. ...................................... 222/39; 222/43; 222/50; 222/95; 222/105; 222/386.5; 128/214 F
[58] Field of Search ....... 128/214 F, 214 E, DIG. 12; 222/41, 43, 44, 47, 49, 50, 95, 105, 386.5, 154, 158, 39

[56] References Cited

U.S. PATENT DOCUMENTS

| 1,750,979 | 3/1930 | Webb | 222/41 |
| 3,425,415 | 2/1969 | Gordon et al. | 222/41 |
| 3,561,644 | 2/1971 | Works et al. | 222/95 |
| 3,640,277 | 2/1972 | Adelberg | 222/386.5 |
| 3,774,603 | 11/1971 | McPhee | 222/158 |
| 4,014,010 | 3/1977 | Jinotti | 128/214 E |

Primary Examiner—H. Grant Skaggs
Attorney, Agent, or Firm—McAulay, Fields, Fisher, Goldstein & Nissen

[57] ABSTRACT

Apparatus for the parenteral fluid administration to a patient including a pressure applying piston to apply pressure to a flexible bag containing the parenteral fluid. The piston has an indicator to indicate its movement and stop devices are provided which can be adjustably positioned to give the piston a predetermined movement to dispense a predetermined quantity of fluid.

7 Claims, 3 Drawing Figures

CONSTANT FEED DEVICE

This invention relates to a constant feed device, particularly a constant feed device in the medical field, such as in drip units for infusion of a liquid into the vein of a patient.

BACKGROUND OF THE INVENTION

In drip feed units, it is a virtual requirement that there be a constant flow or drip into the patient. This ensures that the patient is under a constant state of medication. If the rate of medication is not uniform, and if drugs are used which have a short half life, then quite often the patient is placed in a condition of alternatively being over treated and under treated, and often with the consequences of over treatment having side effects and undesirable reactions.

One form of drip device is the use of a bottle or bag which is held in an elevated position, and wherein the flow is regulated by an adjustable clamp on the hose to the cannula in the patient's vein. The flow of such a unit varies due to the varying pressure head of the liquid, the flow decreasing as the liquid falls in level in the reservoir or bag or bottle.

Sophisticated units are available, these including electrically driven units, but with any electrical device, severe insulation requirements have to be met to prevent even small current leakages measured in microamps which could be detrimental to a patient's heart.

Other forms of devices are known, such as disclosed in U.S. Pat. Nos. 3,895,741, 4,033,479 and West German Pat. No. 2,731,448 in which the liquid to be dispensed is provided in a pliant bag, and a pressure applying means in the form of a piston or diaphragm pressurizes the liquid to dispense the liquid to be infused into the patient.

However, during the infusion of drugs or any liquid into a patient, it is essential that not only must the rate of infusion be closely monitored, but also the total dose be carefully controlled. Also it is essential that no air be infused at any time.

SUMMARY OF THE INVENTION

It is an object of this invention to provide an infusion device, or for the administration of parenteral fluid to a patient, in which the administration can be carefully controlled, not only as to the rate, but also to the dose or quantity.

A further object is to provide such an apparatus which can be preset to deliver a specific quantity at a specific rate.

A still further object is to provide an apparatus which can be portable, and also to give a warning when the administration is completed.

Hence there is provided according to the invention an apparatus for the administration of parenteral fluid, said apparatus comprising a container adapted to support a pliant bag containing a liquid to be administered and pressure applying means to apply a pressure to the bag to force the liquid therefrom, the pressure applying means being a rigid piston having a head and elongate body portion of lesser diameter than the head, a flexible diaphragm connected to the container to form an enclosed pressure area on one side of the piston to roll on the elongate body portion of the piston, with the pliant bag situated on the other side of the piston, and adjustable pressure regulating means to admit fluid pressure to the enclosed pressure area.

DESCRIPTION OF THE PREFERRED EMBODIMENT

Figure 1:
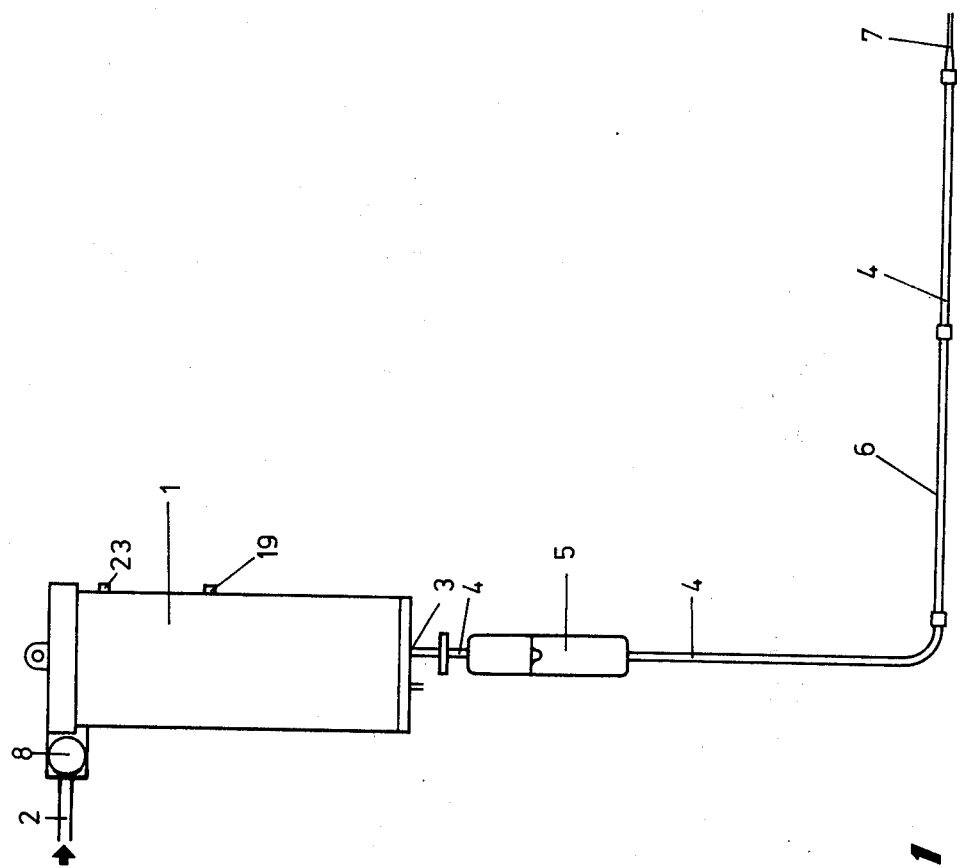
FIG. 1 is a schematic view of the feed device connected for use.

Referring firstly to FIG. 1, the constant feed device 1 is provided with an inlet 2 for a source of pressurizing gas at one end of the device, and at the other end is provided with an outlet 3 connected by tube 4 to a bubble trap 5. A further tube 4 connects the trap 5 to a fixed flow restrictor 6 before a further tube 4 connects to the infusion needle 7.

The inlet 2 is connected to pressure reducing valve and regulator 8 which may be adjusted and preset as desired, the pressure selected being determined by the viscosity of the fluid being infused, and also the size and length of the fixed restrictor 6. This restrictor can in its simplest form be a tube having a selected size and length, so that the flow therethrough is determined by the pressure of the fluid delivered by valve 8, the viscosity and the restrictor 6.

Hence the desired flow rates for various fluids can be precalculated, and the operator can then select the desired pressure and the correct restrictor from the known calculations.

Figure 2:
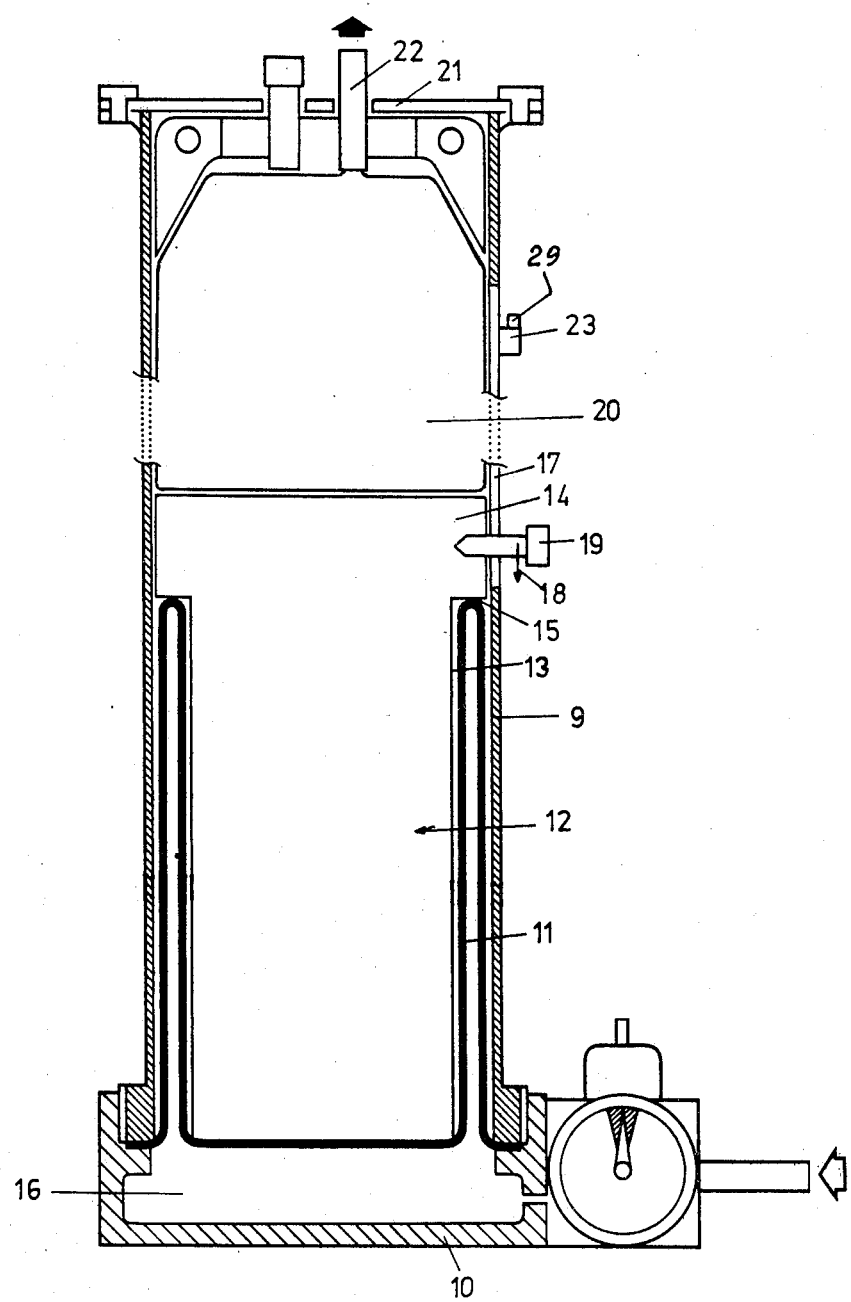
FIG. 2 shows one form of constant feed device.

The feed device 1 can feed from the bottom thereof as shown in FIG. 1, or can feed from the top as shown in FIG. 2, it being realized that by using the device of FIG. 2, that this overcomes the problem of varying flow due to the varying head of fluid in the device.

The unit 1 comprises a cylinder 9 having a base 10, and clamping therebetween a flexible diaphragm 11. A piston 12, freely movable in the cylinder 9 is adapted to be supported by and moved by the diaphragm 11. Preferably as shown the piston 12 has a portion 13 depending from the head 14 of the piston, with the diaphragm 11 rolling and unrolling about the flange 15.

The base 10 has attached thereto an adjustable constant pressure valve 8 which is adapted to pass constant fluid pressure to the chamber 16 below the diaphragm 11.

The cylinder 9 can be of any suitable material, either metal or one of the rigid plastics materials, and preferably can be transparent so that the interior thereof may be viewed.

As shown in FIG. 2, the cylinder 9 can have a longitudinal slot 17 extending along its upper portion of a length corresponding to the stroke of the piston.

An indicator 18 such as a pointer held by a stud or screw 19 is attached to the head of the piston and cooperates with a graduated scale on the cylinder.

The upper portion of the cylinder is adapted to receive a pliant bag of fluid to be dispensed and infused into the patient, the bag 20 being inserted through a quick opening lid 21 at the end of the cylinder, the bag 20 having its outlet 22 extending through the lid 21.

Towards the upper end of the slot 17 there is provided a stop 23, this stop having preferably incorporated therewith an alarm or other signal device 30, to stop the piston at the desired time to ensure that the piston stops when the bag is empty and to ensure that no air is dispensed. Adjustable stops can also be positioned along the slot 17, so that the piston will stop when a desired quantity of fluid has been dispensed.

Figure 3:
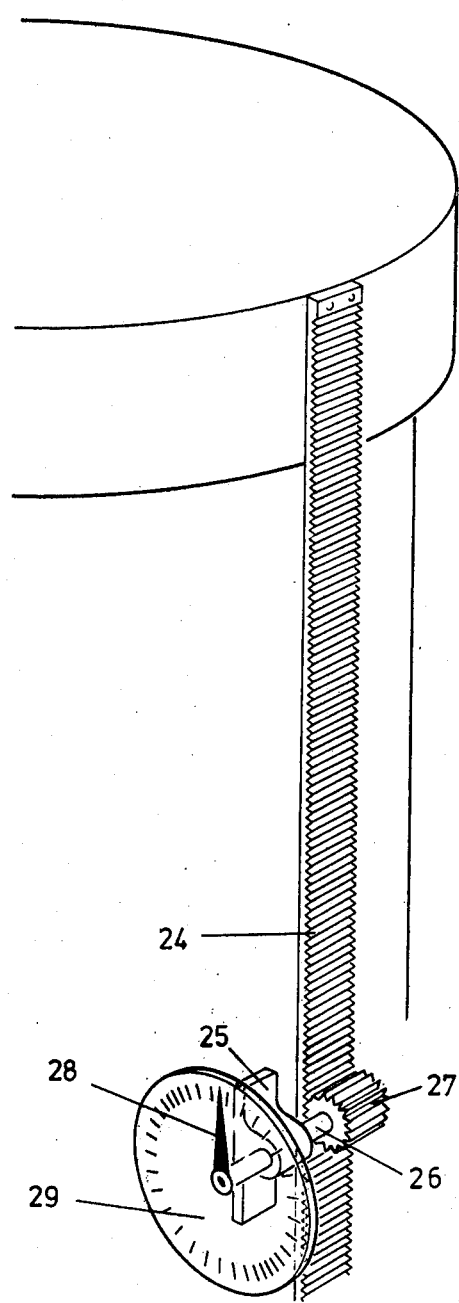
FIG. 3 shows an alternate form of the device.

An alternative form of the invention is shown in FIG. 3 which will give a more accurate indication of the amount of fluid dispensed. In this embodiment, the piston has attached thereto by studs or rivets a member in the form of a rack 24 which is adapted to slide in the slot 17. The rack 24 has teeth and mounted on the cylinder 9 is a housing 25 carrying a shaft 26 on which is mounted a pinion 27 engaging the teeth of the rack 24.

The other end of the shaft 26 is connected either directly or through gearing to a pointer 28 moving over scale 29 to give an amplified indication of the piston movement.

The source of fluid pressure can be of any regular supply of $O_2$, N, $CO_2$ or other supply of fluid pressure in a hospital operating theatre or the like.

In the line of feed from the flexible bag 20 to the patient, there is provided the calibrated flow restriction device 6, so that as the liquid is under a constant head due to the constant pressure, and as the calibrated flow restrictor device has a constant aperture therethrough, the desired constant flow rate is achieved.

The calibrated flow restrictor 6 can be a small cylindrical unit having the desired hole or aperture therethrough, so that in order to change the flow rate it is merely necessary to replace the flow restrictor with one of the required calibration.

Thus, it will be seen that as there is a constant pressure applied to the liquid in the flexible bag or container, that there is in effect a constant head on the liquid to flow through the calibration device in order to ensure the desired uniform flow.

With this form of unit, the constant flow can be achieved by connection to the normal pressurized supply of gas which is available, either from a gas bottle or from some pressurized source, and the folded diaphragm ensures that the piston moves in the container in a free and non-sticking manner.

The container can be formed of a clear material such as glass or one of the rigid plastics material, or a clear window like area can be provided in one side of the container so that the users of the unit can readily determine the amount of liquid remaining in the container.

Adjustable stop means can be provided to engage the slot, and in its simplest form can comprise a stud engaging a sleeve or small nut engaging the interior of the cylinder wall through the slot, so that by loosening the stud, the stop can be repositioned.

In a further alternative, the device could be incorporated in a portable unit, so that a patient can receive medication whilst ambulatory. A small pressurized source of air or other gas or a spring loaded pressure source can be used, which can be "loaded" on pre-tensioned or pre-pressurized by any means for example manually.

This would be a small lightweight device, and a smaller sachet or bag of fluid can be infused in this instance.

In another form of the invention, there can be provided a linear caliper device mounted on the container adjacent the viewing slot or aperture through which the piston can be viewed.

The linear caliper can be positioned, and preferably adjustably positioned on the container such that the fixed arm of the caliper can be positioned to indicate the position of the piston at the beginning of the infusion period. After a certain period of time, or any desired period of time, the movable arm of the caliper can then be positioned to indicate the new position of the piston, and the distance between the two arms of the caliper can then be read and by having the graduations on the caliper suitably pre-calibrated, the quantity infused can be readily determined.

In order to take a further reading at a later date, either the reading at the present is noted and this compared with a reading at the later time, or alternatively the caliper is positioned so that the fixed arm of the caliper is positioned to coincide with the position of the piston and thus the latter reading can be taken in the same manner as the earlier reading.

Preferably, the caliper is a slide caliper, and it can be mounted in brackets or the like screwed or other wise affixed to the container wall. The caliper can be positioned adjustably in the brackets so that the fixed arm can be positioned as desired on the piston at the beginning of the infusion period.

The reading of the position of the piston can be taken from a suitable point or surface on the piston, or alternatively the piston can be provided with a suitable line or mark or the like.

Although a linear caliper has been described as being suitable for the purpose, other forms of measuring devices can be provided in order to measure the movement of the piston over a certain period of time, from which the rate of infusion can be readily calculated.

Also, the piston can incorporate in conjunction with the surrounding cylinder or casing an adjustable stop or the like, so that where a certain quantity of liquid is to be infused, the stop can be positioned to contact the piston when that desired quantity has been infused to prevent the further movement of the piston. This is particularly advantageous where for example a certain quantity of drug has to be infused to a patient such as a baby, and any excess infusion would be detrimental to the baby or patient so that by adjusting the stop the certain quantity can be infused and no further infusion can take place. This is a form of fail-safe device on the unit.

Similarly, the stop can be provided adjustably on the piston for example working on the groove of the piston to contact the abutment on the casing, alternatively the adjustment could be by a movable abutment on the casing. In this connection also it is desirable that infusion terminate before all the liquid has been dispensed from the bag or container in order to prevent the infusion of air into the patient, and in this respect a stop can be provided on the device so that infusion cannot proceed past a certain point so that at all times there is sufficient quantity of liquid in the bag to prevent the accidental infusion of any air.

It is also to be realised with the present invention that while conventional pistons are circular, that with the present invention the piston can be of a shape other than circular, for example square or the like so that if the infusing liquid is packaged in a square container this can be readily positioned into the square casing.

It is to be realised also that other forms of pistons and shapes of pistons can be utilized with the present invention.

The piston can be driven by any suitable form, such as a spring, or air pressure or any driving force such as a weight or the like. In this connection, also in order to provide complete portability of the infusing apparatus, the piston could be propelled by a portable source of pressurized fluid, such as a small carbon dioxide cylinder. In this way the unit can be particularly effective as a portable unit for use in emergencies, ambulances and the like, or even transporting the patient through a hospital from one locality to another.

The restriction for determining the flow can be any form of device and in one preferred form the restriction could be provided by a tubular portion of a syringe, or even by a hypodermic needle itself.

Also, it is to be realised that a bubble trap is provided so that an air interface is available to prevent the accidental passage of any air bubbles through the unit into the patient.

Also, in accordance with the invention, the pressure release valve is situated and designed to blow off into the atmosphere, so that even if there is an accidental increase in pressure, there is no chance of any of this excessive pressure being applied to the piston or the like in order to give an increase in infusion rate.

Also, an alarm could be triggered by any sudden fall or decrease in fluid pressure, so that when this alarm sounds the attending staff are warned that infusion has ceased, this preferably being incorporated in the valve.

We claim:

1. Apparatus for the administration of parenteral fluids, said apparatus comprising
    a container adapted to support a pliant bag containing a liquid to be administered,
    pressure applying means to apply a said bag including an outlet means, pressure to said bag to force the liquid therefrom,
    said pressure applying means being a rigid piston having a head and elongate body portion of lesser diameter than said head,
    a flexible diaphragm connected to said container to form an enclosed pressure area on one side of said piston to roll on said elongate body portion of said piston, with said pliant bag situated on the other side of said piston, and
    adjustable pressure regulating means to admit fluid pressure to said enclosed pressure area.

2. Apparatus as defined in claim 1 wherein said outlet means includes
    an outlet on said bag through which the liquid is forced, and
    a fluid flow restrictor connected to said outlet.

3. Apparatus as defined in claim 1 or 2, wherein
    at least a portion of the container wall is transparent whereby the piston and plaint bag may be viewed.

4. Apparatus as defined in claim 1 or 2, wherein
    said diaphragm has cylindrical walls and is attached at one end of said container and including:
    a longitudinal slot in a wall of said container, and
    indicator means on said piston protruding through said slot to cooperate with a scale on said container wall.

5. Apparatus as defined in claim 4, including stop means engageable in said slot to limit movement of said piston.

6. Apparatus as defined in claim 1, including
    stop means to prevent movement of said piston at the discharge end of its stroke, and
    alarm means associated with said stop means.

7. Apparatus as defined in claim 1, including
    a longitudinal slot in said cylinder,
    a longitudinal strip attached to said piston and associated with said slot,
    a pinion mounted on said cylinder exterior wall, said pinion being connected to an indicating needle traversing over a scale, and
    teeth on said strip engageable with said pinion.

* * * * *